(12) United States Patent
Hickman et al.

(10) Patent No.: US 11,443,085 B2
(45) Date of Patent: Sep. 13, 2022

(54) MODEL FOR FLUID AND MASS TRANSPORT IN A RECIRCULATING MICROFLUIDIC SYSTEM

(71) Applicant: University of Central Florida Research Foundation, Inc., Orlando, FL (US)

(72) Inventors: James Hickman, Orlando, FL (US); Kazi Tasneem, Orlando, FL (US); Christopher Long, Oviedo, FL (US)

(73) Assignee: UNIVERSITY OF CENTRAL FLORIDA RESEARCH FOUNDATION, INC., Orlando, FL (US)

( * ) Notice: Subject to any disclaimer, the term of this patent is extended or adjusted under 35 U.S.C. 154(b) by 684 days.

(21) Appl. No.: 16/381,660

(22) Filed: Apr. 11, 2019

(65) Prior Publication Data
US 2019/0318054 A1 Oct. 17, 2019

Related U.S. Application Data

(60) Provisional application No. 62/655,909, filed on Apr. 11, 2018.

(51) Int. Cl.
*G06F 30/23* (2020.01)
*B01L 3/00* (2006.01)
*G06F 111/20* (2020.01)

(52) U.S. Cl.
CPC ............ *G06F 30/23* (2020.01); *B01L 3/5023* (2013.01); *B01L 3/5027* (2013.01); *C12Q 2565/629* (2013.01); *G06F 2111/20* (2020.01)

(58) Field of Classification Search
CPC .... G06F 30/23; G06F 2111/20; B01L 3/5027; B01L 3/5023; C12Q 2565/629; G01N 33/52; G01N 33/53
See application file for complete search history.

(56) References Cited

U.S. PATENT DOCUMENTS

| | | | |
|---|---|---|---|
| 7,171,983 B2* | 2/2007 | Chien | B01L 3/502715 137/565.29 |
| 8,748,180 B2 | 6/2014 | Shuler et al. | |
| 9,205,396 B2 | 12/2015 | Arai | |
| 2008/0177518 A1* | 7/2008 | Krishnamoorthy | G06F 30/20 703/9 |

(Continued)

FOREIGN PATENT DOCUMENTS

WO 2018038987 A1 3/2018

OTHER PUBLICATIONS

Kallio. "Paul Octavian Bolcos Evaluation of Mixing Efficiency in a Microfluidic Cartridge Using a Finite Element Method Approach". Examiner and topic approved by the Faculty Council of the Faculty of Natural Sciences. Aug. 12, 2015. 77 Pages. (Year: 2015).*

(Continued)

*Primary Examiner* — Eunhee Kim
(74) *Attorney, Agent, or Firm* — Meunier Carlin & Curfman LLC

(57) ABSTRACT

Disclosed herein are microfluidic systems with recirculation of fluid and computer-implemented methods of calculating conditions within the microfluidic systems. The microfluidic systems include a computing device and a microfluidic device having first and second reservoirs, at least one chamber, and a fluid path connecting the first reservoir, the chamber, and the second reservoir. The methods for calculating conditions include receiving a first reservoir fluid volume, a second reservoir fluid volume, a first concentration, and a second concentration. The methods further include receiving a time-dependent imposed pressure difference between the first reservoir and the second reservoir, then determining a hydraulic pressure difference and an effective pressure difference. The effective pressure difference is used to account for reactions occurring within the microfluidic device and to determine the value of the condition within the microfluidic device. Methods of perform- (Continued)

ing an experiment using a microfluidic device with recirculation are also disclosed herein.

20 Claims, 6 Drawing Sheets

(56) References Cited

U.S. PATENT DOCUMENTS

2015/0219622 A1    8/2015  Hickman
2018/0320125 A1*  11/2018  Levner ................ C12N 5/0688

OTHER PUBLICATIONS

Oliveira et al. "Simulations of extensional flow in microrheometric devices". Microfluid Nanofluid (2008) 5:809-826. DOI 10.1007/s10404-008-0277-5. (Year: 2008).*
Orabona et al. "Numerical Optimization of a Microfluidic Assisted Microarray for the Detection of Biochemical Interactions". Sensors 2011, 11, 9658-9666; doi:10.3390/s111009658 . (Year: 2011).*
Perestrelo et al. "Microfluidic Organ/Body-on-a-Chip Devices at the Convergence of Biology and Microengineering". Sensors 2015, 15, 31142-31170; doi:10.3390/s151229848. (Year: 2015).*
Oleaga, C. et al. 2016 "Multi-Organ toxicity demonstration in a functional human in vitro system composed of four organs," Scientific Reports, 6: 20030.
Wang, Y. et al 2016. "Microfluidic blood-brain barrier model provides in vivo-like barrier properties for drug permeability screening" Biotechnology and Bioengineering.
Esch, M et al. 2016. Modular, pumpless body-on-a-chip platform for the co-culture of GI tract epithelium and 3D primary liver tissue. Lab on a Chip, 16: 2719.

* cited by examiner

MODEL FOR FLUID AND MASS TRANSPORT IN A RECIRCULATING MICROFLUIDIC SYSTEM

CROSS REFERENCE TO RELATED APPLICATIONS

This application claims benefit of U.S. Provisional Application No. 62/655,909, which was filed Apr. 11, 2018, the contents of which are hereby incorporated in their entirety.

STATEMENT REGARDING FEDERALLY FUNDED RESEARCH

This invention was made with government support under Grant no. R01NS050452 awarded by the National Institutes of Health. The government has certain rights in the invention.

BACKGROUND

The major research uses of animals are both in assessing potential toxicity of chemicals and in drug testing. Animal tests often are long in duration, expensive, and raise ethical issues. Further, animal tests are not always predictive of human response. In terms of human response to environmental toxicants, it is not ethically possible to conduct direct tests on humans, and extrapolation of animal results to human response is problematic. Over-regulation results in unnecessary expense; under-regulation endangers human health and the environment, so better testing systems are necessary.

In vitro tests can supplement and may reduce dependency on animal tests. However, in vitro tests fail to capture many important aspects of human and mammalian response to chemicals. Most in vitro tests are based on the use of multi-well plates where isolated cells or tissues are placed in medium spiked with a bolus dose of the test chemical. Such systems miss key aspects of physiological response. For example, the dose dynamics in the body differ considerably from static systems as time-dependent changes in chemical concentration occur in the body at a tissue site due to the processes controlling absorption, distribution, metabolism and excretion of a compound. Further, static well systems typically use a single cell or tissue type; in the body, metabolites are exchanged between different tissue/organ compartments. Even if multiple tissue types were represented in a single well, the ratio of one tissue to another and the nature of the circuits connecting them can alter the time-dependent concentration of the metabolites. In addition to these factors, single cells in a well, in most cases, do not represent functional tissues or subsystems of the body, nor experience the mechanical forces the cells in the body do, particularly those associated with fluid flow, and these mechanical forces are known to alter gene expression and metabolism of many chemicals. Microfluidic devices can be used to more accurately simulate true physiological systems, enabling continuous flow of media past a cell culture and more accurately simulating physiological dose dynamics. These devices can be built to incorporate compartments with different cell types or engineered organs.

SUMMARY

While microfluidic devices are able to more accurately simulate true physiological systems than static well cell cultures, there is a difficulty in assessing conditions within a microfluidic device at a microscopic level, particularly when the microfluidic system recirculates fluid. For example, reactions within the microfluidic device can be highly localized. A metabolite created by a cell culture in one chamber may become bound or react with an enzyme or cell in a separate chamber, leading to disparities in local concentrations of the metabolite across the microfluidic device. Flow rates can also change based on the structure of a particular chamber, leading to a poorly defined shear stress acting upon cell cultures or other surface components within the device. The lack of understanding of these conditions leads to expensive trial-and-error based experimentation. Thus, in the technical environment of recirculating biomedical microfluidics, there is a need for systems that can pinpoint highly localized concentrations and flow rates using fluid and mass transport modeling.

For body-on-a-chip biomedical microfluidic systems, different organs are represented by different units of the microfluidic. Recirculation within a biomedical microfluidic is desirable for several reasons. First, recirculation of the media enables interaction between the various units of a biomedical microfluidic system in a bidirectional manner. By contrast, systems with no recirculation enable interaction only in a unidirectional manner (that is, an upstream unit affects a downstream unit, but the downstream unit does not affect the upstream unit). Additionally, recirculation enables the units of a biomedical microfluidic to interact with each other over a longer time frame, such that slow interactions (e.g., slow chemical reactions) can build up over time and affect the other units. For body-on-a-chip systems, bidirectional and long term interactions between units are important to accurately simulate the body because recirculation of blood enables interactions among organs in complex and time-dependent manners.

Disclosed herein are microfluidic systems with recirculation of fluid and computer-implemented methods of calculating conditions within the microfluidic systems. The microfluidic systems include a microfluidic device and a computing device. The microfluidic device includes a fluid, first and second reservoirs, at least one chamber in fluid communication with the first reservoir and the second reservoir, and a fluid path connecting the first reservoir, the chamber, and the second reservoir. The computing device includes a processor and a memory that is operably connected to the processor. The memory includes computer-executable instructions that cause the processor to carry out the methods for calculating the conditions within the microfluidic device.

Methods for calculating conditions within the microfluidic device having recirculation are also disclosed herein. Conditions can include, but are not limited to, the concentration of a component at a specific spatial location, a concentration profile over a specified spatial region, an effective flow rate of the fluid between the first and second reservoirs, mass transport of chemical species or suspended components (e.g., particles) from one chamber to another, shear stresses on units/objects/tissues in the microfluidic device, shear rates, shear stresses at the material interfaces, flow rates among the microfluidic chambers, and the average molecular velocity of the component. The methods for calculating conditions include receiving, at the processor, a first reservoir fluid volume and a second reservoir fluid volume. The methods further include receiving a first concentration, which is the concentration of a component in a first reservoir, and a second concentration, which is the concentration of the same component in a second reservoir. The methods further include receiving a time-dependent imposed pressure difference between the first reservoir and the second reservoir, then determining a hydraulic pressure difference and an effective pressure difference, which is based on the imposed and hydraulic pressure differences. The effective pressure difference is used to account for reactions occurring within the microfluidic device and to determine the value of the condition within the microfluidic device.

Methods of performing an experiment using a microfluidic device with recirculation are also disclosed herein. The methods include setting a desired value for a condition within the microfluidic device, performing a calculation that accounts for an effective pressure difference between the first reservoir and the second reservoir and reactions occurring within the microfluidic device, and determining a set of initial conditions for achieving the desired value.

It should be understood that the above-described subject matter may also be implemented as a computer-controlled apparatus, a computer process, a computing system, or an article of manufacture, such as a computer-readable storage medium.

Other systems, methods, features and/or advantages will be or may become apparent to one with skill in the art upon examination of the following drawings and detailed description. It is intended that all such additional systems, methods, features and/or advantages be included within this description and be protected by the accompanying claims.

BRIEF DESCRIPTION OF THE DRAWINGS

The components in the drawings are not necessarily to scale relative to each other.

DETAILED DESCRIPTION

Unless defined otherwise, all technical and scientific terms used herein have the same meaning as commonly understood by one of ordinary skill in the art. Methods and materials similar or equivalent to those described herein can be used in the practice or testing of the present disclosure. As used in the specification, and in the appended claims, the singular forms "a," "an," "the" include plural referents unless the context clearly dictates otherwise. The term "comprising" and variations thereof as used herein is used synonymously with the term "including" and variations thereof and are open, non-limiting terms. The terms "optional" or "optionally" used herein mean that the subsequently described feature, event or circumstance may or may not occur, and that the description includes instances where said feature, event or circumstance occurs and instances where it does not. Ranges may be expressed herein as from "about" one particular value, and/or to "about" another particular value. When such a range is expressed, an aspect includes from the one particular value and/or to the other particular value. Similarly, when values are expressed as approximations, by use of the antecedent "about," it will be understood that the particular value forms another aspect. It will be further understood that the endpoints of each of the ranges are significant both in relation to the other endpoint, and independently of the other endpoint. As used herein, "operably connected" means that the particular elements are connected in such a way that they cooperate to achieve their intended function or functions. The "connection" may be direct, indirect, physical, or remote.

Example Microfluidic Devices

Figure 1:
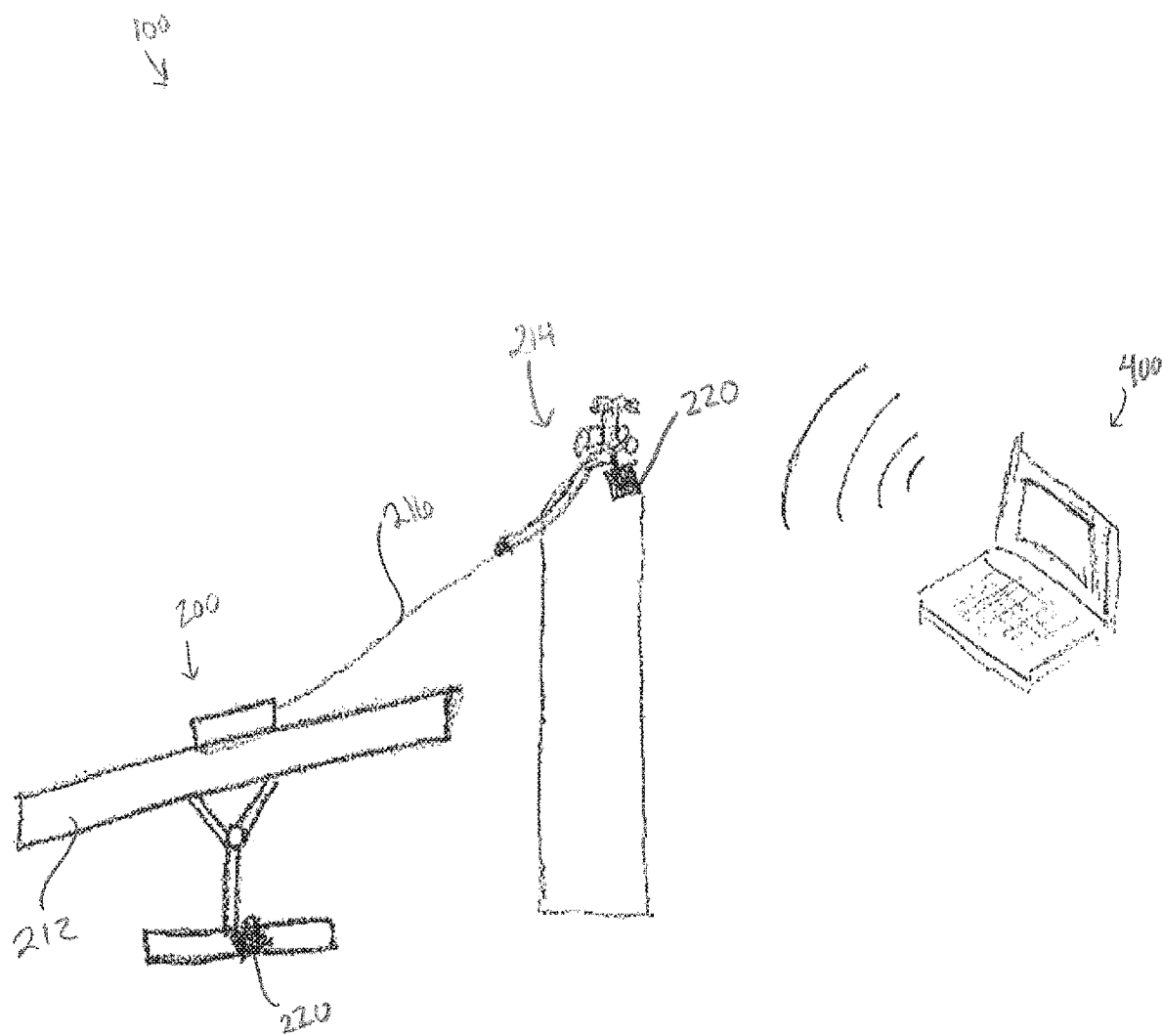
FIG. 1 shows an example implementation of a microfluidic system including a microfluidic device with recirculation, a tilting platform, a pneumatic system, and a computing device.
Figure 2:
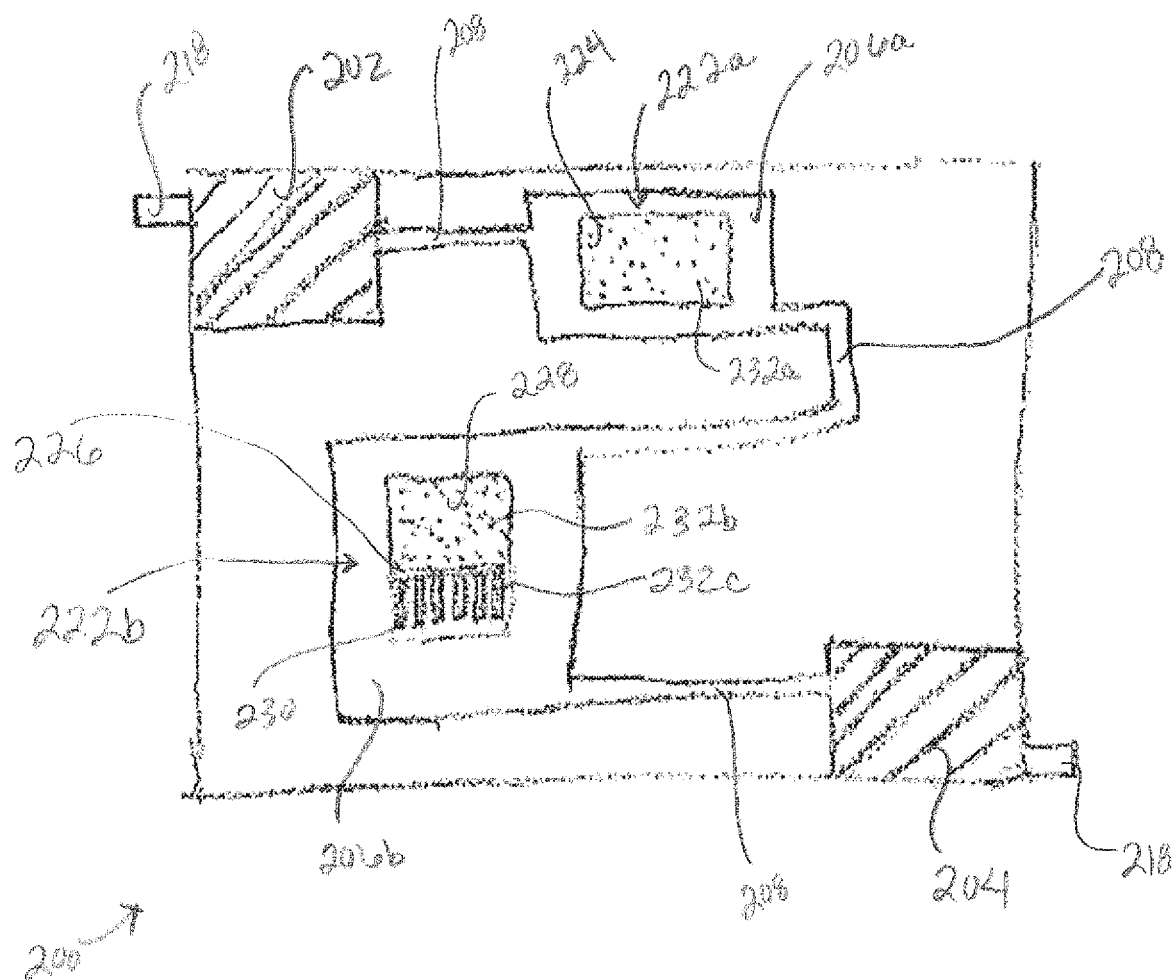
FIG. 2 shows an example implementation of a microfluidic device.
Figure 3:
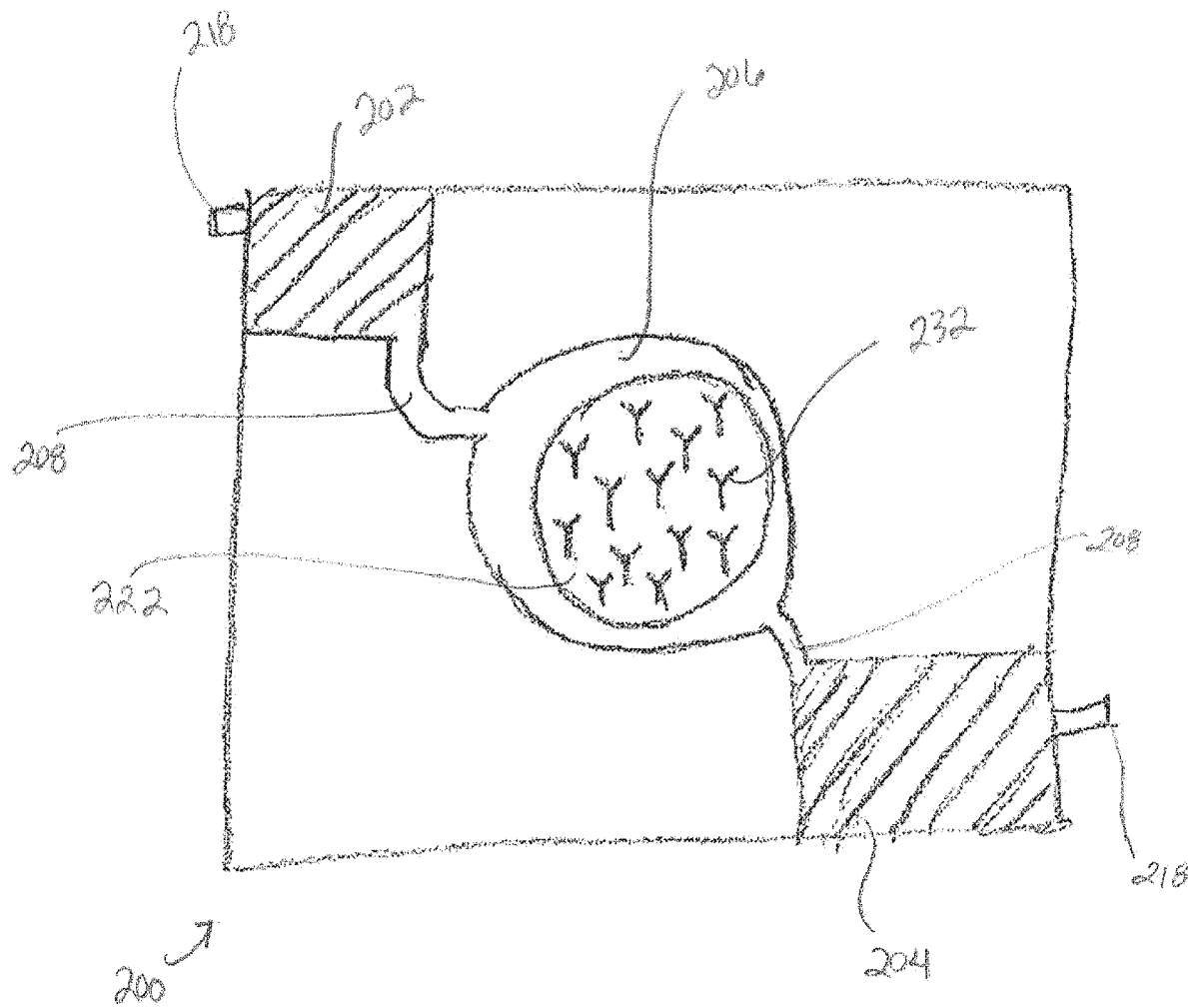
FIG. 3 shows another example implementation of a microfluidic device.

Disclosed herein are microfluidic systems with recirculation of fluid and computer-implemented methods of calculating conditions within the microfluidic systems. As shown in FIG. 1, microfluidic system 100 include a microfluidic device 200 and a computing device 400. Exemplary microfluidic devices 200 are shown in FIGS. 2 and 3. The microfluidic devices 200 include first and second reservoirs 202, 204, one or more chambers 206 in fluid communication with the first reservoir 202 and the second reservoir 204, a fluid path 208 connecting the first reservoir 202, the chamber(s) 206, and the second reservoir 204, and a fluid that flows along the fluid path 208 between the first reservoir 202, the chamber(s) 206, and the second reservoir 204 (fluid not shown). Ports 218 may be used to deliver any fluid (liquid or gas) to the device 200. Ports 218 are shown as being fluidically connected to reservoirs 202, 204. However, ports 218 can be connected at any position on the microfluidic device 200. In some implementations, ports 218 can be used to connect microfluidic devices to each other in series, such that the recirculating fluid is shared across devices.

In some implementations, the microfluidic system 100 can include a tilting platform 212, as shown in FIG. 1. The microfluidic device 200 is placed upon the tilting platform 212 to create gravitational pressure differences that result in flow of the fluid within the microfluidic device 200. Alternatively, or in addition, a pneumatic pressure system 214 can impose hydraulic pressure on the fluid within the microfluidic device 200, causing fluid flow. In one example, the pneumatic pressure system 214 can include tubing 216 to connect to a port 218 on the microfluidic device 200. In some implementations, one or more controllers 220 can be included to receive instructions from computing device 400 regarding the imposed pressure difference and to regulate the pressure difference that is imposed upon the fluid, either by altering the tilting of platform 212 or by regulating the pneumatic pressure system 214.

The fluid of the microfluidic system 100 can include one or more components at any desired concentration. In some implementations, the components can be cells suspended within the fluid. The component could also be any large or small molecule, including polypeptides, polynucleotides, metabolites, cytokines, media reagents, enzymes, and antibodies. For example, in some implementations, the fluid is a serum-free medium, and the components include ingredients of the serum-free medium.

As shown in FIGS. 2 and 3, the microfluidic device can include one or more chambers 206 (e.g., chambers 206a, 206b in FIG. 2 or chamber 206 in FIG. 3). The chambers can, for example, include one or more functional units 222 that can include cells or other biologically reactive surface components as described below. In some implementations, the functional units 222 can be considered to be analogous to a tissue, or they can play a role in a simulated organ or organ system. In some implementations, a functional unit 222 can include a surface, substrate, container or three-dimensional construct for cells (i.e., in which cells are contained, grown, acted on and/or maintained). For example, the microfluidic device 200 shown in FIG. 2 comprises a first functional unit 222a comprising a liver cell culture housed within a three-dimensional construct 224. Fluid, for example, a serum-free cell culture media, from the first reservoir 202 enters a first chamber 206a containing the three-dimensional construct 224 to deliver nutrients to the liver cell culture housed therein. The fluid exits the first chamber 206a via fluid path 208 and enters a second chamber 206b housing a second functional unit 222b that comprises a neuromuscular junction 226 between a culture of motoneurons on a microelectrode array 228 and a muscle cell culture on a cantilever array 230. The first and second chambers 206a, 206b are collectively referred to herein as chambers 206. International Patent Application No. PCT/US17/47085 and U.S. Patent Application Publication No. 2015/0219622 teach microfluidic systems comprising a variety of example functional units, and are each incorporated by reference in their entireties.

A surface component 232 can be attached to any two or three-dimensional surface within the microfluidic device. The surface component can react with components of the fluid, for example, cells, polypeptides, polynucleotides, metabolites, cytokines, media reagents, enzymes, and antibodies. In some implementations, the surface component 232 is part of a functional unit 222. In some implementations, such as the one shown in FIG. 2, the surface component 232 is a cell or cell culture (such as the liver cells 232a within three-dimensional construct 224, the motoneurons 232b on the microelectrode array 228, or the muscle cells 232c on the cantilever array 230). The surface component 232 can be, for example, immobilized antibodies (as shown in FIG. 3), immobilized enzymes, or any other molecule, peptide, or protein that can react with components of the fluid.

Example Computing Devices

Figure 4:
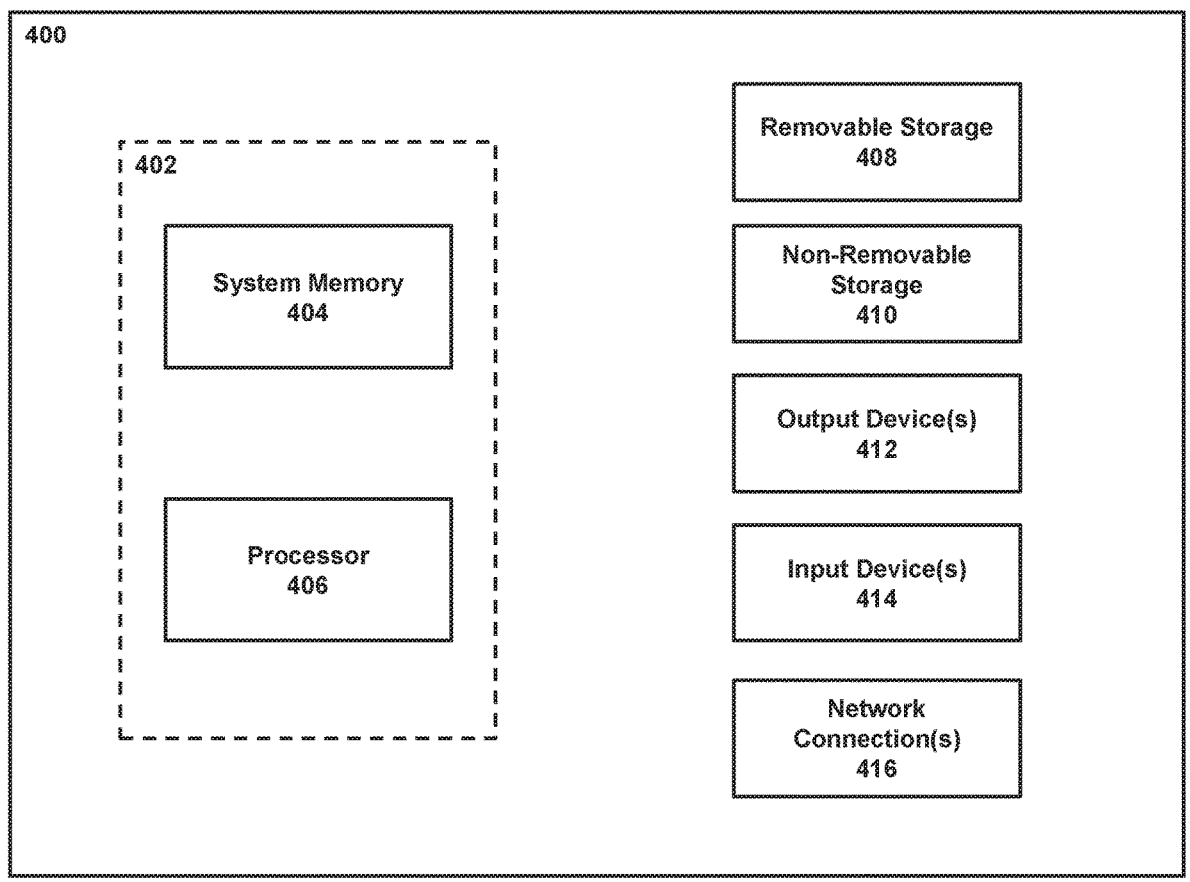
FIG. 4 shows a schematic of a computing device.

A schematic of the computing device 400 is shown in FIG. 4. The computing device 400 includes a processor 406 and a memory 404 that is operably connected to the processor 406. The memory includes computer-executable instructions that cause the processor 406 to carry out the methods for calculating the conditions within the microfluidic device. It should be appreciated that the logical operations described herein with respect to the various figures may be implemented (1) as a sequence of computer implemented acts or program modules (i.e., software) running on a computing device (e.g., the computing device described in FIG. 4), (2) as interconnected machine logic circuits or circuit modules (i.e., hardware) within the computing device and/or (3) a combination of software and hardware of the computing device. Thus, the logical operations discussed herein are not limited to any specific combination of hardware and software. The implementation is a matter of choice dependent on the performance and other requirements of the computing device. Accordingly, the logical operations described herein are referred to variously as operations, structural devices, acts, or modules. These operations, structural devices, acts and modules may be implemented in software, in firmware, in special purpose digital logic, and any combination thereof. It should also be appreciated that more or fewer operations may be performed than shown in the figures and described herein. These operations may also be performed in a different order than those described herein.

Referring to FIG. 4, an example computing device 400 upon which implementations of the invention may be implemented is illustrated. It should be understood that the example computing device 400 is only one example of a suitable computing environment upon which implementations of the invention may be implemented. Optionally, the computing device 400 can be a well-known computing system including, but not limited to, personal computers, servers, handheld or laptop devices, multiprocessor systems, microprocessor-based systems, network personal computers (PCs), minicomputers, mainframe computers, embedded systems, and/or distributed computing environments including a plurality of any of the above systems or devices. Distributed computing environments enable remote computing devices, which are connected to a communication network or other data transmission medium, to perform various tasks. In the distributed computing environment, the program modules, applications, and other data may be stored on local and/or remote computer storage media.

In its most basic configuration, computing device 400 typically includes at least one processor 406 and system memory 404. Depending on the exact configuration and type of computing device, system memory 404 may be volatile (such as random access memory (RAM)), non-volatile (such as read-only memory (ROM), flash memory, etc.), or some combination of the two. This most basic configuration is illustrated in FIG. 4 by dashed line 402. The processor 406 may be a standard programmable processor that performs arithmetic and logic operations necessary for operation of the computing device 400. The computing device 400 may also include a bus or other communication mechanism for communicating information among various components of the computing device 400.

Computing device 400 may have additional features/functionality. For example, computing device 400 may include additional storage such as removable storage 408 and non-removable storage 410 including, but not limited to, magnetic or optical disks or tapes. Computing device 400 may also contain network connection(s) 416 that allow the device to communicate with other devices. Computing device 400 may also have input device(s) 414 such as a keyboard, mouse, touch screen, etc. Output device(s) 412 such as a display, speakers, printer, etc. may also be included. The additional devices may be connected to the bus in order to facilitate communication of data among the components of the computing device 400. All these devices are well known in the art and need not be discussed at length here.

The processor 406 may be configured to execute program code encoded in tangible, computer-readable media. Tangible, computer-readable media refers to any media that is capable of providing data that causes the computing device 400 (i.e., a machine) to operate in a particular fashion. Various computer-readable media may be utilized to provide instructions to the processor 406 for execution. Example tangible, computer-readable media may include, but is not limited to, volatile media, non-volatile media, removable media and non-removable media implemented in any method or technology for storage of information such as computer readable instructions, data structures, program modules or other data. System memory 404, removable storage 408, and non-removable storage 410 are all examples of tangible, computer storage media. Example tangible, computer-readable recording media include, but are not limited to, an integrated circuit (e.g., field-programmable gate array or application-specific IC), a hard disk, an optical disk, a magneto-optical disk, a floppy disk, a magnetic tape, a holographic storage medium, a solid-state device, RAM, ROM, electrically erasable program read-only memory (EEPROM), flash memory or other memory technology, CD-ROM, digital versatile disks (DVD) or other optical storage, magnetic cassettes, magnetic tape, magnetic disk storage or other magnetic storage devices.

In an example implementation, the processor 406 may execute program code stored in the system memory 404. For example, the bus may carry data to the system memory 404, from which the processor 406 receives and executes instructions. The data received by the system memory 404 may optionally be stored on the removable storage 408 or the non-removable storage 410 before or after execution by the processor 406.

It should be understood that the various techniques described herein may be implemented in connection with hardware or software or, where appropriate, with a combination thereof. Thus, the methods and apparatuses of the presently disclosed subject matter, or certain aspects or portions thereof, may take the form of program code (i.e., instructions) embodied in tangible media, such as floppy diskettes, CD-ROMs, hard drives, or any other machine-readable storage medium wherein, when the program code is loaded into and executed by a machine, such as a computing device, the machine becomes an apparatus for practicing the presently disclosed subject matter. In the case of program code execution on programmable computers, the computing device generally includes a processor, a storage medium readable by the processor (including volatile and non-volatile memory and/or storage elements), at least one input device, and at least one output device. One or more programs may implement or utilize the processes described in connection with the presently disclosed subject matter, e.g., through the use of an application programming interface (API), reusable controls, or the like. Such programs may be implemented in a high level procedural or object-oriented programming language to communicate with a computer system. However, the program(s) can be implemented in assembly or machine language, if desired. In any case, the language may be a compiled or interpreted language and it may be combined with hardware implementations.

Example Methods

Figure 5:
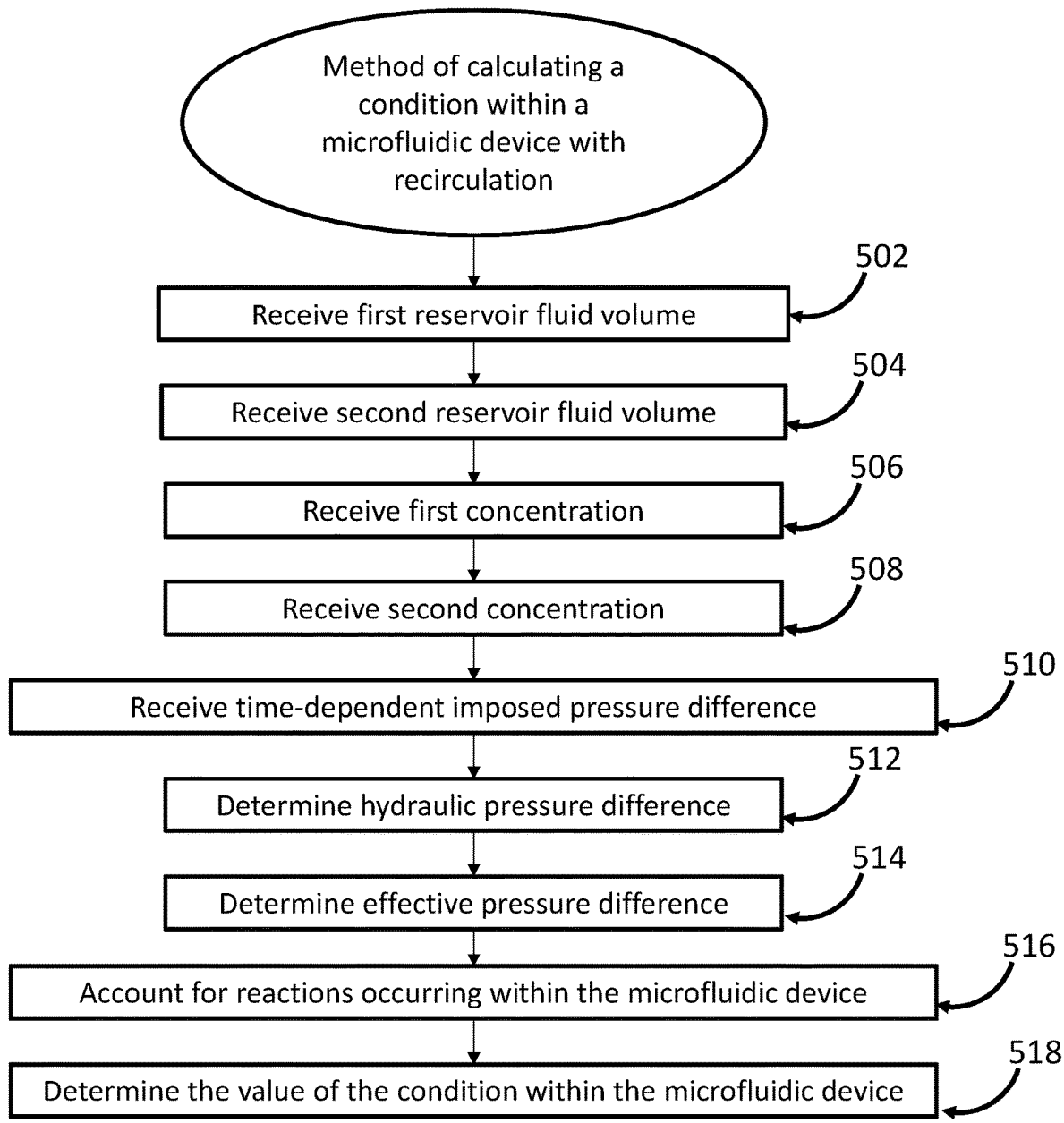
FIG. 5 shows a flow chart illustrating a method of calculating a condition within a microfluidic device having recirculation according to an implementation described herein.

A flow chart of an example method for calculating a condition within a microfluidic device having recirculation is shown in FIG. 5. As used herein, the term "receive" can refer to the receipt of external or internal inputs by the processor 406. For example, in some implementations, the processor 406 receives an external input of the first reservoir fluid volume from a user such as a researcher who is planning an experiment. It should be understood that the user can provide such information using the input device 414. In some implementations, the processor 406 receives an internal input of the first reservoir fluid volume as part of a larger, iterative method, for example, when attempting to find the necessary initial condition (the first reservoir fluid volume) to obtain a desired value of a condition within the microfluidic device (which will be described below). Conditions being calculated can include, but are not limited to, the concentration of a component at a specific spatial location, a concentration profile over a specified spatial region, an effective flow rate of the fluid between the first and second reservoirs, mass transport of chemical species or suspended components (e.g., particles) from one chamber to another, shear stresses on units/objects/tissues in the microfluidic device, shear rates, shear stresses at the material interfaces, flow rates among the microfluidic chambers, and the average molecular velocity of the component. The methods for calculating conditions include step 502 of receiving (at the processor 406) a first reservoir fluid volume and step 504 of receiving a second reservoir fluid volume. The method further includes step 506 of receiving a first concentration, which is the concentration of a component in a first reservoir. As described above, a component is any cell or molecule (large or small), including polypeptides, polynucleotides, metabolites, cytokines, enzymes, and antibodies. The method also includes step 508 of receiving a second concentration, which is the concentration of the same component in the second reservoir. The methods further include step 510 of receiving a time-dependent imposed pressure difference between the first reservoir and the second reservoir, step 512 of determining a hydraulic pressure difference, and step 514 of determining an effective pressure difference. The hydraulic pressure difference is based on a first volumetric height of fluid in the first reservoir and a second volumetric height of fluid in the second reservoir, and the effective pressure difference is which is based on the imposed and hydraulic pressure differences. The effective pressure difference is used in step 516 when accounting for reactions occurring within the microfluidic device that deplete or increase the first and second concentrations of the component. Finally, in step 518, the value of the condition within the microfluidic device is determined.

In some implementations of the methods, the imposed pressure difference changes over at least one time step. The processor can receive the imposed pressure difference, the first reservoir fluid volume, the second reservoir fluid volume, the first concentration, and the second concentration before the time step (or before and after the time step) to determine the value of the condition. In some implementations, the value of the condition is iteratively determined before and after each of a plurality of time steps. The change in the imposed pressure difference can follow a regular waveform, such as a sawtooth, sinusoidal, or square waveform. Alternatively, the imposed pressure difference can follow a non-regular pattern. For example, the timing of the tilting platform 212 shown in FIG. 1 can be set to cause a regular or non-regular change in the imposed pressure by changing the gravitational forces that affect the flow of the fluid within the device. Alternatively, or in addition, a pneumatic pressure system 214 can be set to cause a regular or non-regular hydraulic pressure change within the microfluidic system. In some implementations, the computing device 400 can relay a desired imposed pressure difference to one or more controllers 220, which then impose the time-dependent pressure difference onto the fluid.

The methods disclosed herein account for reactions occurring within the device when calculating the value of the condition within the recirculating microfluidic device. The reaction can be a reaction of a component within the fluid, either via surface reactions, volume reactions, or bulk reactions. Surface or volume reactions include any reaction taking place at any two or three-dimensional surface or construct within the microfluidic device. In some implementations of the method, surface or volume reactions are assigned rate constants for calculation purposes. The reaction can take place directly between a component of the fluid and the surface (i.e. adsorption/absorption), or the reaction can take place between a component of the fluid and a surface component 232 that is attached to any surface within the microfluidic device (for example, the binding of a component of the fluid to the antibodies/surface component 232 of FIG. 3). Surface or volume reactions can be based on, or affected by, the surface or volume density of the surface component 232, the surface area, the spatial location of the surface within the microfluidic device, the concentration of the component at the specific spatial location of the surface, a concentration profile over a specified spatial region around the surface, an effective flow rate of the fluid between the first and second reservoirs, time dependent mass transport rates, time dependent shear rates, time dependent shear stresses, time dependent flow rates of fluid among the microfluidic chambers, and the average molecular velocity of the component in the fluid. Surface or volume reactions can result in the generation or depletion of a biological molecule. The biological molecule can be, for example, a product of an immobilized enzyme. The biological molecule can also be, for example, cytokines or metabolites produced by a cell culture on a surface within the microfluidic device. For example, in the microfluidic device 200 shown in FIG. 2, the liver cell culture in three-dimensional construct 224 can generate metabolites that then are depleted by the motoneurons on the microelectrode array 228 and/or the muscle cells on the cantilever array 230. The metabolites could also be adsorbed to the surfaces of the chambers 206, the fluid path 208, or the first and second reservoirs 202, 204. All of these surface or volume reactions are accounted for in the method of calculating the value of a condition within the recirculating microfluidic device.

Bulk reactions include reactions that take place within the fluid. For example, bulk reactions can occur between a first component of the fluid and any other component of the fluid. The reactions can be reversible or irreversible. The bulk reactions can be based on, or affected by, one or more of the following variables: the concentration of the component at the specific spatial location within the fluid, a concentration profile over a specified spatial region within the fluid, an effective flow rate of the fluid between the first and second reservoirs, time dependent mass transport rates, time dependent shear rates, time dependent shear stresses, time dependent flow rates of fluid among the microfluidic chambers, and the average molecular velocity of the component.

Some implementations of the methods include accounting for convection or diffusion of the component. Convection or diffusion can be affected by one or more of the following variables: the spatial location within the fluid, the concentration of the component at the specific spatial location within the microfluidic device, a concentration profile over a specified spatial region within the fluid, an effective flow rate of the fluid between the first and second reservoirs, time dependent mass transport rates, time dependent shear rates, time dependent shear stresses, time dependent flow rates of fluid among the microfluidic chambers, the average molecular velocity of the component, and bulk or surface or volume reactions taking place within the microfluidic device. This can include determining a variable diffusion-like term. The diffusion-like term can be determined, for example, for at least one specific spatial location within the microfluidic device. In some implementations, the flow rate/fluid velocity for at least one specific spatial location is accounted for when determining the diffusion-like term. When the imposed pressure difference changes over at least one time step, convection or diffusion can be accounted for before (or before and after) the at least one time step.

In some implementations, the method of calculating the value of a condition includes using a finite element method with boundary conditions. In some implementations, the boundary condition is a value of a condition that was determined by the method in a previous time step. The boundary conditions are determined using analytical calculations, or determined via calculations from the previous time step of the finite element method. The boundary conditions can be set, for example, for an opening between at least one of the first or second reservoir. The boundary conditions can include, for example, the imposed pressure difference, the effective pressure difference, the effective flow rate within the device, the first reservoir fluid volume, and/or second reservoir fluid volume. For example, the boundary conditions can depend, at least in part, on a hydrodynamic pressure difference (e.g. the difference in height between the two reservoirs, either due to different volumes, different heights on a tilting platform, or a combination thereof). In some implementations, the boundary conditions include the first concentration (of the component in the first reservoir), the second concentration (of the component in the second reservoir), or both. The first concentration, the second concentration, or both can be determined, for example, using a volume weighted average of i) the concentration of the component in the volume of fluid flowing into or out of the first or second reservoir, and ii) the previous first concentration, the previous second concentration, or both. In some implementations, a diffusion-like term is incorporated into the finite element method.

In some implementations, the value of the condition is determined using analytical methods. In some implementations, the condition is modeled using a first order differential equation. The first order differential equation is directly solved in the time domain, or an analytical solution can be determined in the frequency domain after performing a Fourier transform. The variable diffusion-like term, described above, can be modeled within the analytical methods using ordinary differential equations. In some implementations of the analytical methods, the chamber is modeled as a fluid resistor and the first and second reservoirs are modeled as capacitors. The modeling of the first and second reservoirs can include incorporating a first order differential equation into the analytical methods. In some implementations, the calculations can be performed in a simulation software program, for example, a software program that employs principles of electrical circuit analysis.

Figure 6:
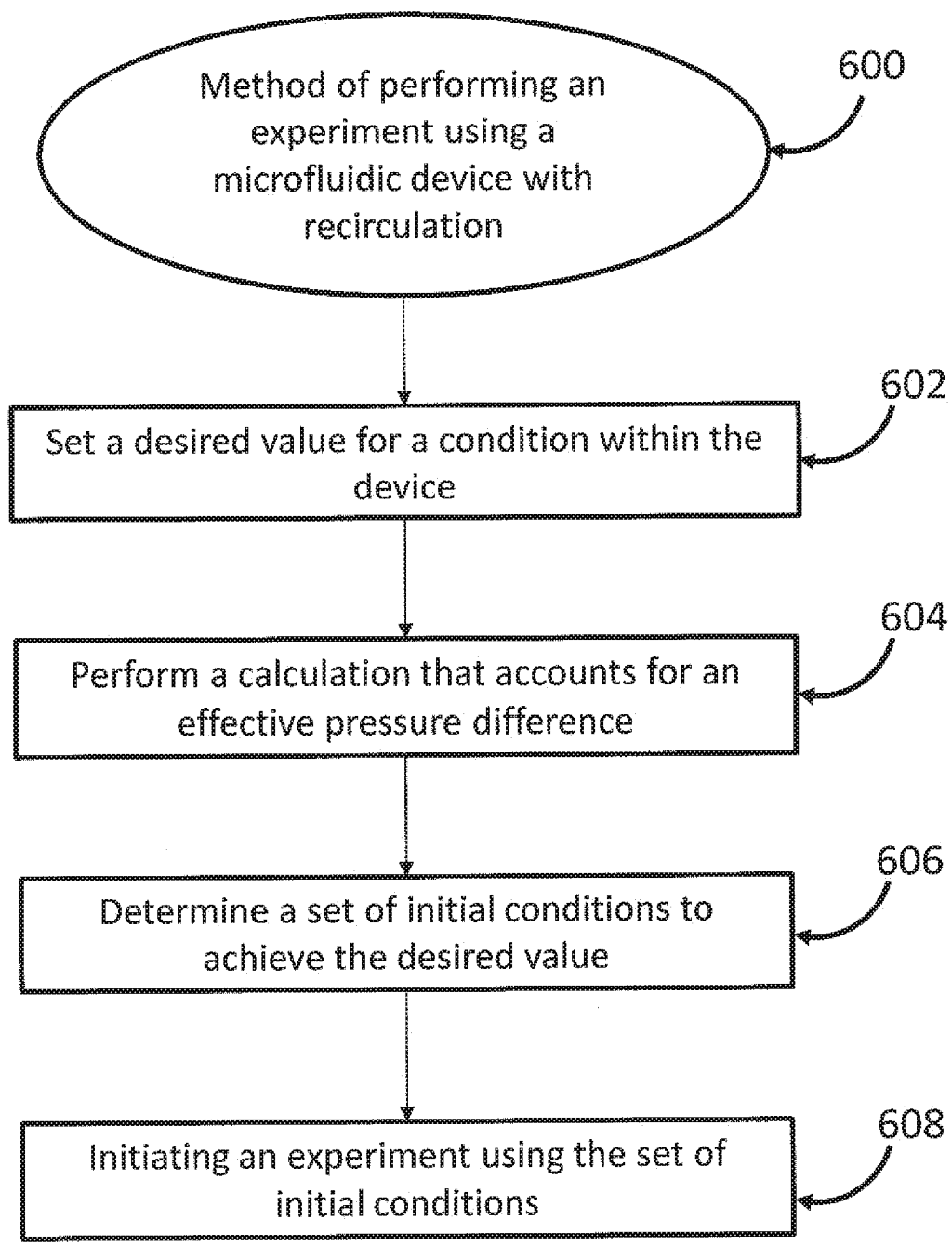
FIG. 6 shows a flow chart illustrating a method of performing an experiment using a microfluidic device having recirculation according to an implementation described herein.

Methods of performing an experiment using the recirculating microfluidic devices are also disclosed herein. A flow chart schematic of an exemplary method 600 is shown in FIG. 6. The methods include step 602 of setting a desired value for a condition within the microfluidic device, step 604 of performing a calculation that accounts for an effective pressure difference between the first reservoir and the second reservoir and reactions occurring within the microfluidic device, and step 606 of determining a set of initial conditions for achieving the desired value. The set of initial conditions can include one or more of a first reservoir fluid volume, a second reservoir fluid volume, a first concentration of a component in the first reservoir, a second concentration of the component in the second reservoir, and a time dependent imposed pressure difference. The initial conditions are then used to initiate the experiment in step 608. Initiating the experiment can include mixing the component into a solution to create a first fluid having the determined first concentration of the component. Initiating the experiment can further include adding a first volume of the first fluid to the first reservoir (the first volume of the first fluid being equivalent to the determined first reservoir fluid volume). In some implementations, initiating the experiment can include mixing the component into a solution to create a second fluid having the determined second concentration of the component and adding a second volume of the second fluid to the second reservoir (the second volume of the second fluid being equivalent to the determined second reservoir fluid volume). Finally, initiating the experiment can include imposing the determined time dependent imposed pressure difference to initiate circulation and recirculation of the fluid. In some implementations, performing the experiment further comprises sending instructions from a processor to a controller to cause the controller to impose the determined time dependent imposed pressure difference on the fluid.

Although the subject matter has been described in language specific to structural features and/or methodological acts, it is to be understood that the subject matter defined in the appended claims is not necessarily limited to the specific features or acts described above. Rather, the specific features and acts described above are disclosed as example forms of implementing the claims.

Example

Models and algorithms for fluid and mass transport with bulk and surface reactions in recirculating microfluidic systems are described below. The microfluidic systems utilize recirculation of fluid via, for example, an oscillatory pressure differential between two or more fluidic reservoirs. This device is a microfluidic device containing fluid paths and chambers of larger volumes with the chambers enabling the incorporation of various functional units. A functional unit can be a construct that is either responsive to environmental conditions, influences environmental conditions, or affects the fluidics within the system. For instance, a functional unit can include enzymes, catalysts, immobilized reactants or sensors. This system has applications for body-on-a-chip (or organ-on-a-chip) devices, in which the functional units inside the chambers are cultures of cells and/or bioMEMS devices or environmental sensors (e.g. dissolved gasses, soluble compounds, ions, pH, etc.). In some implementations, the fluid of the system a serum-free medium.

The oscillatory pressure differential used to drive the fluidic flow may be imposed by a tilting platform to produce gravitational pressure differences, gas pressure to produce hydraulic pressure differences, or any such system that produces a time dependent oscillatory pressure differential. The imposed gravitational or hydraulic pressure may have any regular profile (eg sawtooth, sinusoidal, square wave, etc) or even a random or non-regular profile that varies in time. This profile need not return to the original position, such that the recirculation of fluid may not be a complete recirculation. Additionally, this method and algorithm may be used for modeling fluid and mass transport for a portion of an oscillatory cycle, a profile with a single change of pressure, or any other profile that does not oscillate but which has an imposed pressure that has at least one period of time in which the pressure is different from the initial condition.

The algorithm described herein incorporates finite volumes and concentrations in two or more fluidic reservoirs as well as the time dependent imposed pressure differential. Because the reservoirs have finite volumes of fluid and the microfluidic device has a fluidic resistance to flow, the effective pressure difference between the two or more reservoirs is not linearly proportional to the imposed pressure differential. Instead, the effective pressure differential, which controls the flow rate through the system, is dependent on the time-dependent profile of imposed pressure differential and the time-dependent hydraulic pressure difference between the reservoirs caused by the difference in volumetric height between the two reservoirs. The mass transport through the system is related to the flow rates in the system as well as the concentrations of the components in the reservoirs and throughout the microfluidic device. In particular, the finite reservoir volumes with finite concentrations of chemical components influences the mass transport through time dependent flow and through mixing and time-dependent concentrations within the reservoirs due to fluid flowing into and out of these reservoirs. Additionally, reactions occurring in the system are modeled and both influence the overall mass transport and are influenced by the microfluidic mass transport. These reactions may be surface reactions (e.g. immobilized enzyme on a surface or monolayer of cells), reactions in certain volumes (e.g. immobilized enzyme in a 3D construct or material, or cells suspended in a 3D construct or material such as a hydrogel or other biomaterial scaffold), or bulk reactions (e.g. conjugation of two or more compounds in solution, or reactions between two or more soluble components). Adsorption and absorption of compounds to the microfluidic device are modeled, and are also influenced by and influence the mass transport throughout the system. Additionally, these reactions and adsorption/absorption may occur within the microfluidic device (including the fluidic channels and chambers) or within the reservoirs. For analytical purposes, the fluidic channels and chambers (which do not vary in volume of fluid over time) can behave as resistive elements to fluidic flow, while the reservoirs, which have a time-dependent volume of fluid, can have a first order differential equation component to the fluidic response, and can act similar to a capacitor.

The algorithm can be enacted in in at least two ways: 1) computationally calculated during each time step of a computational fluid dynamics or finite element method analysis of the system or 2) calculated analytically using equations analogous to resistive and capacitive elements.

In an example implementation of the computational calculation, in each iteration, the imposed driving pressure difference P(t) (e.g. hydrodynamic pressure from tilting the device causing a difference in height between two or more reservoirs) is altered by the hydrodynamic pressure difference between the two or more reservoirs caused by the difference in volumes in the reservoirs. This altered pressure difference is then imposed as boundary conditions on the computational model at locations where liquid flows into and out of the reservoirs into the microfluidic device. Additionally, the concentrations of chemical components in the reservoirs are imposed on the same boundaries to define the concentrations of these components in the fluid flowing into the microfluidic device. The volume for each reservoir for the next time step in the computational analysis is calculated from the volumetric flow during the time step through the boundary between the reservoir and the microfluidic device. The concentration of the components in the fluid flowing through these same boundaries is used along with the change in volume to determine the new concentrations of components within the reservoirs by performing a volume-weighted average of the previous concentrations in the reservoir with the concentrations in the volume of fluid flowing into or out of the reservoir.

In an example implementation of the analytical calculation, the effective pressure differences between reservoirs and effective flow rates are modeled using first order differential equations either directly solving the differential equation in the time domain, determining the analytical solution in the frequency domain after a Fourier transform, or performing these calculations in a simulation software that incorporates these calculations (e.g. an electrical circuit analysis software). Either the effective pressure differences or the effective flow rates calculated from this method may be imposed on the computational model as boundary conditions to produce equivalent solutions.

For reactions at specific locations (for example, for metabolism of compounds by a liver or other metabolically active construct or the generation of cytokines or other signaling molecules) surface and volume reactions can be imposed on specific surfaces or on volumes representing a three dimensional construct. These reactions have specific rate constants that may occur in a number of forms including zero order, first order, and second order equations, and these reactions may be reversible or irreversible. Adsorption and absorption of compounds onto surfaces and into volumes is also modeled with reversible or irreversible reaction kinetics. Reactions within the bulk of the fluid are also modeled with reversible or irreversible reaction kinetics. The time-dependent flow dynamics and local concentration profiles caused by the reservoir-based microfluidic device influence each of these reactions and dynamics.

In one implementation of the invention, the transport of components within the fluid due to the oscillatory imposed pressure difference is modeled after each oscillation cycle. In this algorithm, the transport within the device during each cycle due to convection and diffusion is modeled using a variable diffusion-like term. This diffusion-like term varies within the model depending on the fluid velocity at a specific physical location over the entire cycle. The velocity profiles throughout the microfluidic device, coupled with the diffusivity of the component within the fluid, are modeled or determined experimentally and then the diffusion-like term as a function of position is determined for each point within the microfluidic device. This diffusion-like term is then used to calculate the transport of components within the fluid over time using ordinary differential equations, and can be calculated analytically or computationally (e.g. finite element analysis). In this implementation, reaction rates and adsorption/absorption reactions are incorporated as above, to produce a model that is capable of modeling the fluid dynamics and mass transport throughout the microfluidic device.

The invention claimed is:

1. A computer-implemented method of calculating a condition within a microfluidic device with recirculation, the method comprising:
   receiving a first reservoir fluid volume,
   receiving a second reservoir fluid volume,
   receiving a first concentration, the first concentration being the concentration of a component in a first reservoir,
   receiving a second concentration, the second concentration being the concentration of the same component in a second reservoir,
   receiving a time-dependent imposed pressure difference between the first reservoir and the second reservoir,
   determining a hydraulic pressure difference, wherein the hydraulic pressure difference is based on a first volumetric height of fluid in the first reservoir and a second volumetric height of fluid in the second reservoir,
   determining an effective pressure difference between the first and second reservoirs, wherein the effective pressure difference is based on the imposed pressure difference and the hydraulic pressure difference,
   using the effective pressure difference, accounting for reactions occurring within the microfluidic device that deplete or increase the first and second concentrations of the component,
   determining a value of the condition within the microfluidic device, and
   controlling an experiment using the microfluidic device with recirculation based on the value of the condition within the microfluidic device.

2. The computer-implemented method of claim 1, wherein the condition is the concentration of the component at a specific spatial location, a concentration profile over a specified spatial region, an effective flow rate of the fluid between the first and second reservoirs, a mass transport property of the component, a shear stress on a unit of the microfluidic device, a shear stress on an object positioned within a unit of the microfluidic device, a shear stress at a material interface, a shear rate within the microfluidic device, a flow rate between two chambers of the microfluidic device, or the average molecular velocity of the component.

3. The computer-implemented method of claim 1, wherein the imposed pressure difference changes over at least one time step.

4. The computer-implemented method of claim 3, further comprising receiving the imposed pressure difference, the first reservoir fluid volume, the second reservoir fluid volume, the first concentration, and the second concentration before the at least one time step.

5. The computer-implemented method of claim 3, wherein the value of the condition is determined before and after the at least one time step.

6. The computer-implemented method of claim 1, wherein accounting for reactions comprises accounting for at least one surface or volume reaction.

7. The computer-implemented method of claim 6, wherein the at least one surface or volume reaction results in the generation or depletion of a biological molecule.

8. The computer-implemented method of claim 6, wherein the at least one surface or volume reaction is a reaction of the component with a surface component that is attached to a surface within the microfluidic device.

9. The computer-implemented method of claim 8, wherein the surface component is selected from a group consisting of an enzyme and a cell.

10. The computer-implemented method of claim 6, wherein the at least one surface or volume reaction is affected by one or more of the following variables: the dimensions of the surface, the spatial location of the surface within the microfluidic device, the concentration of the component at the specific spatial location of the surface, a concentration profile over a specified spatial region around the surface, an effective flow rate of the fluid between the first and second reservoirs, a time dependent mass transport rate, a time dependent shear rate, a time dependent shear stress, a time dependent flow rate of fluid among the microfluidic chambers, and the average molecular velocity of the component.

11. The computer-implemented method of claim 1, wherein accounting for reactions comprises accounting for at least one bulk reaction.

12. The computer-implemented method of claim 11, wherein the at least one bulk reaction is affected by one or more of the following variables: the concentration of the component at the specific spatial location within the fluid, a concentration profile over a specified spatial region within the fluid, an effective flow rate of the fluid between the first and second reservoirs, time dependent mass transport rates, time dependent shear rates, time dependent shear stresses, time dependent flow rates of fluid among the microfluidic chambers, and the average molecular velocity of the component.

13. The computer-implemented method of claim 1, further comprising accounting for convection or diffusion of the component.

14. The computer-implemented method of claim 13, wherein convection or diffusion is affected by one or more of the following variables: the spatial location within the fluid, the concentration of the component at the specific spatial location within the microfluidic device, a concentration profile over a specified spatial region within the fluid, an effective flow rate of the fluid between the first and second reservoirs, time dependent mass transport rates, time dependent shear rates, time dependent shear stresses, time dependent flow rates of fluid among the microfluidic chambers, the average molecular velocity of the component, and bulk or surface or volume reactions taking place within the microfluidic device.

15. The computer-implemented method of claim 13, wherein the imposed pressure difference changes over at least one time step, and accounting for convection or diffusion occurs before and after the at least one time step.

16. The computer-implemented method of claim 1, wherein the method further comprises using a finite element method with boundary conditions.

17. The computer-implemented method of claim 16, wherein the boundary conditions are set for an opening between at least one of the first or second reservoir, and wherein the boundary conditions are selected from a group consisting of the imposed pressure difference; the first reservoir fluid volume, the second reservoir fluid volume, or both; the value of a condition determined in a previous time step; and the first concentration, the second concentration, or both.

18. The computer-implemented method of claim 1, wherein the method further comprises determining the value of the condition using analytical methods.

19. The computer-implemented method of claim 18, further comprising at least one chamber in fluid communication with the first reservoir and the second reservoir, and wherein the at least one chamber is modeled as a fluid resistor in the analytical methods.

20. The computer-implemented method of claim 19, wherein the first and second reservoirs are modeled as capacitors in the analytical methods.

\* \* \* \* \*